United States Patent [19]

Cobb et al.

[11] Patent Number: 5,670,686
[45] Date of Patent: Sep. 23, 1997

[54] ALKYL SUBSTITUTED SILOXANES AND ALKYL SUBSTITUTED POLYETHER FLUIDS

[75] Inventors: Vicky Sue Cobb, Elsie, Mich.; Gary Edward LeGrow, Newberry, Fla.

[73] Assignee: Dow Corning Corporation, Midland, Mich.

[21] Appl. No.: 696,417

[22] Filed: Aug. 13, 1996

[51] Int. Cl.$^6$ .................................................. C07F 7/08
[52] U.S. Cl. ..................... 556/445; 556/453; 556/456; 556/465; 556/466
[58] Field of Search ............................ 556/465, 466, 556/445, 453, 456

[56] References Cited

U.S. PATENT DOCUMENTS

| | | | |
|---|---|---|---|
| 3,427,271 | 2/1969 | McKellar | 260/29.2 |
| 4,289,891 | 9/1981 | Brown | 556/453 |
| 5,446,185 | 8/1995 | Cobb et al. | 556/451 |
| 5,448,124 | 9/1995 | Cobb et al. | 556/445 |
| 5,527,935 | 6/1996 | Stepp et al. | 556/445 |

*Primary Examiner*—Paul F. Shaver
*Attorney, Agent, or Firm*—Richard I. Gearhart

[57] ABSTRACT

New alkyl substituted siloxanes and alkyl substituted polyether fluids are prepared by reacting an unsaturated alkyl, a aralkyl or ether with alkylhydrido siloxanes such as (i) comonomers $RSi(OSiMe_2H)_3$, (ii) oligomers $(HMe_2SiO)_2-Si(R)-O-Si(R)-(OSiMe_2H)_2$, and (iii) higher molecular weight siloxane species $RSi[(OSiMe_2)_xOSiMe_2H]_3$ and $[HMe_2SiO(Me_2SiO)_x]_2Si(R)O(R)Si[(OSiMe_2)_xOSiMe_2H]_2$. R is a $C_2$ to $C_{18}$ straight-chain or branched-chain alkyl substituent.

7 Claims, No Drawings

ALKYL SUBSTITUTED SILOXANES AND ALKYL SUBSTITUTED POLYETHER FLUIDS

FIELD OF THE INVENTION

The invention relates to a novel family of alkyl substituted siloxanes and alkyl substituted polyether fluids as new compositions of matter.

BACKGROUND OF THE INVENTION

In U.S. Pat. No. 5,446,185, assigned to the assignee of this invention, there is described a family of new alkylhydrido siloxanes including comonomers of the formula $RSi(OSiMe_2H)_3$, oligomers of the formula $(HMe_2SiO)_2—Si(R)—O—Si(R)—(OSiMe_2H)_2$, and higher molecular weight siloxanes of the formula $RSi[(OSiMe_2)_xOSiMe_2H]_3$ and $[HMe_2SiO(Me_2SiO)_x]_2Si(R)O(R)Si[(OSiMe_2)_xOSiMe_2H]_2$; in which Me is methyl; R is a $C_2$ to $C_{18}$ straight-chain or branched-chain alkyl substituent; and x has a value of 1–200.

In addition, U.S. Pat. No. 5,488,124, assigned to the assignee of this invention, teaches alkylpolyether siloxane compositions, but does not teach the composition of the present invention.

This invention is an improvement on the prior applications in which a new family of alkyl substituted siloxanes and alkyl substituted polyether fluids are provided by hydrosilylation of the alkylhydrido siloxanes in U.S. Pat. No. 5,446,185. These alkyl substituted siloxanes and alkyl substituted polyether fluids are useful in personal care compositions, lubricants, polishes, paint additives, hydrophobing agents, emulsifiers, and polyurethane foam stabilization.

SUMMARY OF THE INVENTION

The invention is directed to new alkyl substituted siloxanes and alkyl substituted polyether fluids. The siloxanes are compounds covered by one of the formulas: $RSi(OSiMe_2Q)_3$, $(QMe_2SiO)_2—Si(R)—O—Si(R)—(OSiMe_2Q)_2$, $RSi[(OSiMe_2)_xOSiMe_2Q]_3$ and $[QMe_2SiO(Me_2SiO)_x]_2Si(R)O(R)Si[(OSiMe_2)_xOSiMe_2Q]_2$. In the formulas, Me is methyl; R is a $C_2$ to $C_{18}$ straight-chain or branched-chain alkyl substituent; x has a value of 1–200; and Q is independently the same or different alkyl, aralkyl, or polyether group, with the proviso that at least one Q is an alkyl, or aralkyl group.

In the case where Q is an alkyl group, Q can be generally described as a linear or branched carbon chain having from 2 to 30 carbon atoms. Preferred alkyl chains are octyl, hexadecyl, octadecyl and tridecyl. Q can also be an aralkyl group, described generally by the formula $(CH_2X)_a—C_6H_5$, where X is hydrogen, or alkyl chain having at least 2 carbon atoms. Preferred aralkyl groups alpha methyl styryl or styryl substituted groups. Q can also be a radical containing polyether groups, such as oxyethylene groups, oxypropylene groups, oxybutylene groups, or any combination of oxyethylene groups, oxypropylene groups, or oxybutylene groups. A representative Q radical is $—(CH_2)_y(OCH_2CH_2)_a(OCH_2CH(CH_3))_b[OCH_2CH(CH_2CH_3)]_cOR'$, where R' can be hydrogen; an alkyl radical such as methyl, ethyl, propyl, or butyl; an aryl radical such as phenyl; an aralkyl radical such as benzyl; or an acyl radical such as acetyl. The integer y is 3–6; a is 0–120; b is 0–100; and c is 0–50; with the proviso that a, b, and c, cannot all be zero.

The present invention also teaches more efficient process which allows for a one step preparation of alkyl substituted siloxanes and alkyl substituted polyether fluids, rather than the two step process required to achieve complete reaction of the SiH on the siloxane backbone.

It is therefore an object of the present invention to provide a novel family of alkyl substituted siloxanes and alkyl substituted polyether fluids as new compositions of matter.

These and other objects of the present invention will become more apparent from a consideration of the following detailed description thereof.

DETAILED DESCRIPTION OF THE INVENTION

Siloxanes according to the invention can be prepared by hydrosilylation of alkylhydrido siloxanes with alkenyl ether terminated organic oxyalkylene compounds. Alkylhydrido siloxanes such as $RSi(OSiMe_2H)_3$ and $(HMe_2SiO)_2—Si(R)—O—Si(R)—(OSiMe_2H)_2$ can be prepared in high yield by hydrolysis of the corresponding chlorosilanes. Details of the hydrolysis reaction are described in U.S. Pat. No. 5,446,185.

The reaction is briefly depicted in "Scheme 1".

Scheme 1

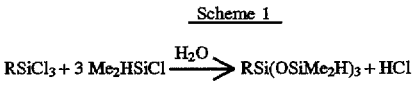

According to "Scheme 1", the amount of $RSi(OSiMe_2H)_3$ obtained in the hydrolysis is dependent upon the temperature at which the reaction is conducted. Where R is n-propyl (Pr), and when the temperature is maintained slightly below 15° C., 83% of the product is $RSi(OSiMe_2H)_3$. At 30° C., 79% of the product is $RSi(OSiMe_2H)_3$; while at 40° C. 47% of the product is $RSi(OSiMe_2H)_3$. At higher temperatures, larger amounts of $(HMe_2SiO)_2—Si(R)—O—Si(R)—(OSiMe_2H)_2$ and higher molecular weight siloxane species are formed.

The products $RSi(OSiMe_2H)_3$ and $(HMe_2SiO)_2Si(R)—O—(R)Si(OSiMe_2H)_2$ from the hydrolysis in "Scheme 1", can be used in the preparation of higher molecular weight siloxane species. The higher molecular weight materials are prepared by an acid catalyzed ring opening of cyclic siloxanes such as a dimethylcyclosiloxane, followed by insertion into $RSi(OSiMe_2H)_3$ and $(HMe_2SiO)_2Si(R)O(R)Si(OSiMe_2H)_2$. Such a process is also described in detail in U.S. Pat. No. 5,446,183 and is briefly depicted below in "Scheme 2".

Scheme 2

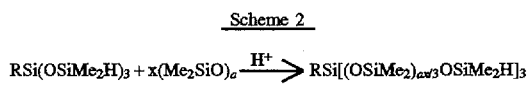

The acid catalyst in "Scheme 2" can be hydrochloric acid, sulfuric acid, phosphoric acid, oxalic acid, acetic acid, trichloroacetic acid, or trifluoromethane sulfonic acid. The method in "Scheme 2" is carried out by creating a mixture of the cyclic siloxane $(Me_2SiO)_a$, $RSi(OSiMe_2H)_3$ or $(HMe_2SiO)_2Si(R)O(R)Si(OSiMe_2H)_2$, (or mixtures of the same), and the acid catalyst. The mixture is heated with agitation at a polymerization reaction temperature, until essentially all of the cyclic siloxane is reacted. The time required will vary depending on the reactants and the reaction conditions. The polymerization reaction in "Scheme 2" is stopped at the desired level of conversion of cyclic siloxane, by using methods known in the art such as neutralization of the catalyst by the addition of an equal, or slightly greater than stoichiometric amount of base. A weak base may be used to neutralize the reaction.

The siloxanes depicted in "Scheme 1" and "Scheme 2" include comonomers, oligomers, and higher molecular weight siloxane species, and are used as intermediates in the preparation of the alkyl substituted siloxanes and alkyl substituted polyether fluids of the invention. The R group in "Scheme 1" and "Scheme 2" is a $C_2$ to $C_{18}$ straight-chain (unbranched) or branched-chain alkyl substituent. Suitable R substituents are ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

The cyclic siloxanes most suitable for "Scheme 2" are (i) hexamethylcyclotrisiloxane with a boiling point of 133 ° C. and the formula [(Me$_2$)SiO]$_3$; (ii) octamethylcyclotetrasiloxane with a boiling point of 171° C. and the formula [(Me$_2$)SiO]$_4$; (iii) decamethylcyclopentasiloxane with a boiling point of 205° C. and the formula [(Me$_2$)SiO]$_5$; and (iv) dodecamethylcyclohexasiloxane with a boiling point of 245° C. and the formula [(Me$_2$)SiO]$_6$.

In the process of preparing the alkyl substituted siloxanes and alkyl substituted polyether fluids of the invention, one or more unsaturated alkyl or aralkyl groups, and possibly an unsaturated polyether are reacted via a hydrosilylation reaction with one of the above described alkylhydrido siloxanes containing the ≡SiH group. In any case, Q will be independently the same or different alkyl, aryl, aralkyl, or polyether group, with the proviso that at least one Q is an alkyl or aralkyl group.

In the case where a particular Q group is an alkyl group, the compositions of the present invention will be prepared by reacting the above described ≡SiH containing siloxanes with an unsaturated alkyl group having from 2 to 30+ carbon atoms.

These unsaturated alkyl groups can be generally represented by the formula:

CH$_2$=CHR' where R' is a linear or branched alkyl group having up to 28 carbon atoms.

Representative Q groups include octyl, dodecyl, hexadecyl, octadecyl and tridecyl.

It is expected that in a give preparation of the compositions of the present invention, that the unsaturated alkyl groups can be the same or different, i.e. be represented by the same or different R' groups.

An example of where the R' groups are the same is illustrated in "Scheme 3".

Scheme 3

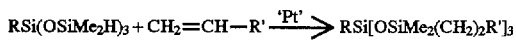

The siloxane portion of the product can be trifunctional, as shown above, or tetrafunctional, as in [R$^1$Me2SiO (SiMe$_2$O)$_x$]$_2$SiR—O—RSi[(OSiMe2)$_x$OSiMe2R$^1$]$_2$. The unsaturated hydrocarbons, R', can be linear or branched alkyl or aralkyl.

In addition, two or more different types of hydrocarbon groups can be attached to the same siloxane to yield a silicone organic copolymer consisting of the branched alkyl (R) siloxane and two different hydrocarbons, R'. An example of how such a material could be prepared is shown in Scheme 4.

Scheme 4

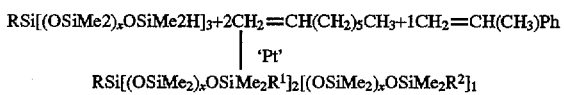

where, for example, R is $C_2$ to $C_{18}$ straight chain or branched alkyl, Me is methyl, Ph is phenyl R$^1$ is (CH$_2$)$_7$CH$_3$ and R$^2$ is (CH$_2$CH(CH$_3$)Ph and these groups are randomly arranged on the siloxane in a ratio of 2:1.

It is also understood that the degree of substitution of the ≡SiH bearing siloxanes will generally be controlled by the ratio of ≡SiH to the alkenyl groups of each different R' group.

Q can also be an organic oxyalkylene group which is alkenyl ether terminated. Suitable compounds contain at least three to about ten carbon atoms in the alkenyl group, and examples of groups which can be used are allyl, isopropenyl, 2-butenyl, 3-butenyl, or hexenyl. Allyl is the most preferred alkenyl group, and representative allyl ether terminated organic oxyalkylene compounds are: H$_2$C=CH—CH$_2$—O—(CH$_2$—CH$_2$O)$_m$—R"; H$_2$C=CH—CH$_2$—O—[CH$_2$—CH(CH$_3$)O]$_n$—R"; and H$_2$C=CH—CH$_2$—O—(CH$_2$—CH$_2$O)$_m$—[CH$_2$—CH(CH$_3$)O]n—R".

In those formulas, m is 1–120; n is 1–100; and R" is hydrogen; an alkyl radical such as methyl, ethyl, propyl, or butyl; an aryl radical such as phenyl; an aralkyl radical such as benzyl; or an acyl radical such as acetyl.

It is preferred to conduct the hydrosilylation reaction with an allyl to ≡SiH ratio of 1.0 to 1.2, although other ratios can be employed. The alkylpolyether siloxane products of the hydrosilylation reaction are best made by reacting the allyl ether of the desired oxyalkylene compound with the corresponding siloxane containing ≡SiH groups. This reaction is best carried out by heating a mixture of the reactants in the presence of a platinum catalyst, such as platinum dispersed on an inert carrier or a compound of platinum such as chloroplatinic acid, at temperatures from 30°–100° C.

The products can be prepared by hydrosilylation of the corresponding alkylhydrido siloxanes with alkenyloxy polyethers and alpha olefins. Representative hydrosilylation reactions according to the invention are depicted in Schemes 5 and 6 as follows:

Scheme 5

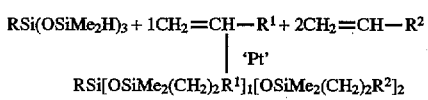

The siloxane portion of the product can be tri-functional, as shown above, or tetrafunctional, as in [R$^1$Me$_2$SiO (SiMe$_2$O)$_x$]$_2$SiR—O—RSi[(OSiMe$_2$)$_x$OSiMe$_2$R$^1$]$_2$. The unsaturated hydrocarbons, R$^1$, can be linear or branched alkyl or aralkyl. The polyethers, R$^2$, can be ethylene oxide, propylene oxide, butylene oxide, or any combination of these. In addition, different types of hydrocarbon groups or polyether groups can be attached to the same siloxane to yield a silicone organic polymer consisting of the branched, alkyl (R) substituted siloxane and two or more different hydrocarbons, R$^1$, or two or more different polyether groups, R$^2$. An example of such a material could be prepared as shown in "Scheme 6".

Scheme 6

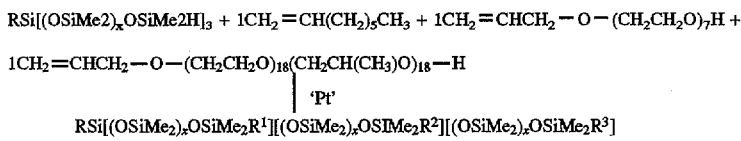

RSi[(OSiMe2)$_x$OSiMe2H]$_3$ + 1CH$_2$=CH(CH$_2$)$_5$CH$_3$ + 1CH$_2$=CHCH$_2$—O—(CH$_2$CH$_2$O)$_7$H +

1CH$_2$=CHCH$_2$—O—(CH$_2$CH$_2$O)$_{18}$(CH$_2$CH(CH$_3$)O)$_{18}$—H

|'Pt'

RSi[(OSiMe$_2$)$_x$OSiMe$_2$R$^1$][(OSiMe$_2$)$_x$OSiMe$_2$R$^2$][(OSiMe$_2$)$_x$OSiMe$_2$R$^3$]

where R$^1$ is (CH$_2$)$_7$CH$_3$, R$^2$ is CH$_2$=CHCH$_2$—O—(CH$_2$CH$_2$O)$_7$H, and R$^3$ is CH$_2$=CHCH$_2$—O—(CH$_2$CH$_2$O)$_{18}$(CH$_2$CH(CH$_3$)O)$_{18}$—H, and these groups are randomly arranged on the siloxane in a ratio of 1:1:1.

The inventors have surprisingly found that the products described herein can be made by a "one step" process, i.e. the hydrocarbon components can be added to the siloxane polymer simultaneously, rather than in two steps. Moreover, only a small excess of the hydrocarbon "Q" groups need to be present during the reaction, as opposed to the large excess of hydrocarbon need to drive the reaction to completion in the prior art.

Hydrosilylation catalysts are well known in the art and the interested reader is referred to the following patents for detailed descriptions regarding their preparation and use: Speier, U.S. Pat. No. 2,823,218; Willing, U.S. Pat. No. 3,419,359; Kookootsedes, U.S. Pat. No. 3,445,420; Polmanteer et al, U.S. Pat. No. 3,697,473; Nitzsche, U.S. Pat. No. 3,814,731; Chandra, U.S. Pat. No. 3,890,359; and Sandford, U.S. Pat. No. 4,123,604. Many of the catalysts known in the art require the reactants to be heated in order for reaction to occur. When such catalysts are employed, this requirement must be taken into consideration.

The concentration of the catalyst may be determined by routine experimentation. Typically, however, the effective amount of catalyst should be in a range so as to provide from about 1-1,000 parts per million (ppm) of platinum by weight in the compositions of the present invention.

This invention is illustrated in more detail in the following examples.

EXAMPLE I

Preparation of PrSi(OSiMe$_2$H)$_3$, n-propyltris(dimethylsiloxy)silane

A mixture of PrSiCl$_3$ (59.92 g, 0.338 moles) and Me$_2$HSiCl (95.90 g, 1.014 moles) was added drop-wise to a 3-necked round bottom flask containing ice water (166.0 g, 9.22 moles). The flask was fitted with a thermometer, a mechanical stirrer, and a pressure equalizing addition funnel. The chlorosilanes were added drop-wise through the addition funnel at a rate to maintain a temperature in the flask slightly below 15° C. The solution was vigorously mixed throughout this addition. The solution was stirred for 30 minutes after completion of the chlorosilane addition. An aqueous layer was drawn off, followed by several NaHCO$_3$ washes, and several water washes until neutral to pH paper. The siloxane was dried over MgSO$_4$ overnight and filtered under N$_2$ pressure, yielding a clear, colorless liquid. The final product contained 83% of PrSi(OSiMe$_2$H)$_3$; 9% of (HMe$_2$SiO)$_2$Si(Pr)—OSi(Pr)(OSiMe$_2$H)$_2$, and 8% of other siloxane impurities. Characterization included Si-29 Nuclear Magnetic Resonance (NMR), Gas Chromatography/Mass Spectrometry (GC/MS), and Gas Chromatography/Flame Ionization Detection (GC/FID).

EXAMPLE II

Example I was repeated, except that room temperature water was used instead of ice water, and the temperature was allowed to rise to 30° C. The final product contained 79% of PrSi(OSiMe$_2$H)$_3$, 12% of (HMe$_2$SiO)$_2$Si(Pr)OSi(Pr)(OSiMe$_2$H)$_2$, and 9% of other siloxane impurities.

EXAMPLE III

Example I was again repeated, except that room temperature water was used instead of ice water, and the temperature was allowed to rise to 40° C. The final product contained 47% of prSi(OSiMe$_2$H)$_3$, 30% of (HMe$_2$SiO)$_2$Si(Pr)OSi(Pr)(OSiMe$_2$H)$_2$, and 23% of other siloxane impurities.

EXAMPLE IV

Preparation of PrSi[(OSiMe$_2$)$_{3.5}$OSiMe$_2$H]$_3$

A solution of n-propyltris(dimethylsiloxy)silane PrSi(OSiMe$_2$H)$_3$ (18.94 g, 0.064 moles) prepared in Example I, (Me$_2$SiO)$_4$ cyclosiloxane (49.82 g, 0.672 moles), and 41 microliters of trifluoromethane sulfonic acid, was heated to 70° C. The flask was fitted with a water cooled condensing column, a magnetic stirrer, and a thermometer. The flask was flushed with N$_2$ prior to heating, followed by N$_2$ positive pressure through the top of the condenser. After heating the flask at 70° C. for four hours, the solution was cooled to room temperature, followed by the addition of NaHCO$_3$ (1.0 g) and diatomaceous earth (Celite) (1.0 g). The mixture was stirred for 4 hours, followed by filtration under N$_2$ pressure, and yielded a clear, colorless liquid. The final average structure determined by Si-29 NMR was (PrSi)$_{1.0}$[(OSiMe$_2$)$_{3.5}$OSiMe$_2$H]$_3$.0. In that structure, the value "1.0" was plus or minus 0.2; the value "3.5" was plus or minus 0.5; and the value "3.0" was plus or minus 0.2. Dimethyl cyclic siloxanes were also present in the product.

EXAMPLE V

Preparation of PrSi{(OSiMe$_2$R$^1$)$_1$(OSiMe$_2$R$^2$)$_2$}, with R$^1$=(CH2)$_7$CH$_3$, and R$^2$=(CH$_2$)$_3$O(CH$_2$CH$_2$O)$_7$H CH$_2$=CHCH$_2$O(CH$_2$CH$_2$O)$_7$H (62.78 g, 0.178 moles) and a platinum catalyst (10 ppm) were placed in a three necked round bottom flask equipped with a thermometer, mechanical stirrer, and a claisen adapter fit with a water cooled condenser and a pressure equalizing addition funnel. Dropwise addition of PrSi(OSiMe$_2$H)$_3$ (27.62 g, 0.086 moles) was adjusted to maintain the temperature below 90° C. throughout the addition. The temperature was maintained at 90° C. for several hours. Dropwise addition of 1-Octene (9.61 g, 0.086) was followed by heating at 100C until no SiH was observed in the InfraRed spectrum. Removal of excess olefin under reduced pressure yielded a clear, liquid. Viscosity was 321 cp.

The following example teaches a one step process for the preparation of alkyl substituted siloxanes and alkyl substituted polyether fluids, rather than the two step process previously described.

EXAMPLE VI

Preparation of PrSi{(OSiMe$_2$)$_6$ (OSiMe$_2$R$^1$)$_1$ (OSiMe$_2$R$^2$)$_2$}, with R$^1$=(CH$_2$)$_7$CH$_3$, and R$^2$=(CH$_2$)$_3$O(CH$_2$CH$_2$O)$_7$H PrSi{(OSiMe$_2$)$_6$(OSiMe$_2$H)}$_3$ (65.87 g, 0.042 moles) and a platinum catalyst (10 ppm) were placed in a three necked round bottom flask equipped with a thermometer, mechanical stirrer, and a claisen adapter fit with a water cooled condenser and a pressure equalizing addition funnel, and heated to 90° C. Dropwise addition of a mixture of $CH_2=CHCH_2O(CH_2CH_2O)_7H$ (30.50 g, 0.083 moles) and 1-octene (6.53 g, 0.058 moles) resulted in an exotherm. The temperature was maintained at 90° C. for four hours, after which additional 1-octene (3.0 g, 0.027) was added to the flask. The solution was heated until the SiH level reached 6 ppm as measured by InfraRed spectroscopy. Removal of excess olefin under reduced pressure yielded a clear, liquid. Brookfield viscosity was 240 cp.

EXAMPLE VII

Preparation of $PrSi(OSiMe_2R)_3$, with $R=(CH_2)_5CH_3$

1-Hexene (55.18 g, 0.657 moles) and a heterogeneous platinum catalyst (50 ppm) were weighed into a three necked round bottom flask equipped with a thermometer, mechanical stirrer, and a claisen adapter fit with a water cooled condenser and a pressure equalizing addition funnel. Dropwise addition of $PrSi(OSiMe_2H)_3$ (54.01 g, 0.182 moles) was adjusted to maintain the temperature below 90° C. throughout the addition. The temperature was maintained at 90° C. until no SiH was observed in the InfraRed spectrum. Removal of excess olefin under reduced pressure, followed by filtration, yielded a clear liquid with solubility in both mineral oil and polydimethylsiloxane. Viscosity was 9.5 cp.

EXAMPLE VIII

Preparation of $PrSi(OSiMe_2R)_3$, with $R=(CH_2)_{30+}CH_3$

C30+ alpha olefin (112.24 g, 0.217 moles) and a heterogeneous platinum catalyst (50 ppm) were weighed into a three necked round bottom flask equipped with a thermometer, mechanical stirrer, and a water cooled condenser. $PrSi(OSiMe_2H)_3$ (17.56 g, 0.055 moles) was added dropwise to the 80° C. mixture. The temperature was increased and maintained at 110° C. until the SiH level was below 5 ppm. Filtration yielded the product, a waxy solid at room temperature. Melting range was 59°–63° C.

EXAMPLE IX

Preparation of $PrSi[(OSiMe_2)_5OSiMe_2R]_3$, with $R=CH_2CH(CH_3)Ph$

Alpha methyl styrene (30.52 g, 0.259 moles) and platinum catalyst were weighed into a three necked round bottom flask equipped with a thermometer, mechanical stirrer, and an addition funnel. $PrSi[(OSiMe_2)_5OSiMe_2H]_3$ (79.66 g, 0..057 moles) was added dropwise to the mixture at a rate to maintain an exotherm, approximately 100° C. The addition funnel was replaced with a water cooled condenser, the temperature was increased to 110° C. and maintained for 2 hours. Removal of excess alpha methyl styrene under reduced pressure resulted in a clear liquid. The material was characterized by FTIR.

EXAMPLE X

Preparation of $Dodecyl-Si[(OSiMe_2R)_3$, with $R=(CH_2)_{17}CH_3$

1-Octadecene (231.04 g, 0.917 moles) and platinum catalyst were weighed into a three necked round bottom flask equipped with a thermometer, mechanical stirrer, and a water cooled condenser. $DodecylSi(OSiMe_2H)_3$ (107.47 g, 0.255 moles) was added dropwise to the mixture at a rate to maintain an exotherm, approximately 110° C. The addition funnel was replaced with a water cooled condenser, the temperature was maintained at 110° C. for 2 hours. Additional 1-octadecene (77.00 g, 0.0.306 moles) was added and the solution was heated at 110° C. until the SiH level was 1 ppm by InfraRed spectroscopy. Removal of excess octadecene under reduced pressure resulted in a golden colored liquid. The final product is a waxy solid.

EXAMPLE XI

Preparation of $PrSi[(OSiMe_2)_5(OSiMe_2R)]_3$, with $R=(CH_2)_{17}CH_3$

1-Octadecene (42.35 g, 0.168 moles) and platinum catalyst were weighed into a three necked round bottom flask equipped with a thermometer, mechanical stirrer, and an addition funnel. $PrSi[(OSiMe_2)_5(OSiMe_2H)]_3$ (64.71 g, 0.047 moles) was added dropwise to the mixture at a rate to maintain the temperature near 90° C. The addition funnel was replaced with a water cooled condenser. The temperature was maintained at 90° C. until the SiH level was below 5 ppm. Removal of excess octadecene under reduced pressure, followed by filtration yielded the product, a clear liquid. Viscosity was 36.1 cp.

EXAMPLE XII

Preparation of $PrSi[(OSiMe_2)_{100}OSiMe_2R]_3$, with $R=(CH_2)_7CH_3$

1-Octene (22.93 g, 0.205 moles) and platinum catalyst were weighed into a three necked round bottom flask equipped with a thermometer, mechanical stirrer, and an addition funnel. $PrSi[(OSiMe_2)_{100}OSiMe_2H]_3$ (982.80 g, 0.051 moles) was added dropwise to the mixture at a rate to maintain the temperature near 90° C. The addition funnel was replaced with a water cooled condenser. The temperature was maintained at 80° C. until the SiH level was below 5 ppm. Removal of excess octene under reduced pressure yielded the product, a clear liquid. Brookfield viscosity of the product was 710 cps.

Other variations may be made in the compounds described without departing from the concept of the invention. The forms of invention described are only exemplary and not intended as limitations on the scope of invention defined in the claims.

That which is claimed is:

1. Compounds selected from the group consisting of $RSi(OSiMe_2Q)_3$, $(QMe_2SiO)_2—Si(R)—O—Si(R)—(OSiMe_2Q)_2$, $RSi[(OSiMe_2)_xOSiMe_2Q]_3$ and $[QMe_2SiO(Me_2SiO)_x]_2Si(R)—O(R)Si[(OSiMe_2)_xOSiMe_2Q]_2$, wherein Me is methyl; R is a $C_2$ to $C_{18}$ straight-chain or branched-chain alkyl substituent; x has a value of 1–200; and Q is independently the same or different alkyl of at least two carbon atoms, aralkyl or polyether group, with the proviso that at least one Q is an alkyl of at least two carbon atoms or aralkyl group.

2. Compounds according to claim 1 in which R is selected from the group consisting of ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl;

3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

3. Compounds according to claim 1, in which at least one Q is an alkyl group having 2 to 80 carbon atoms.

4. Compounds according to claim 1 in which at least one or two Q groups are the same or different polyether having the general formula $-(CH_2)_y(OCH_2CH_2)_a(OCH_2CHCH_3)_b[OCH_2CH(CH_2CH_3)]_cOR'$ wherein R' is hydrogen, an alkyl radical, an aryl radical, an aralkyl radical, or an acyl radical; y is 3–6; a is 0–120; b is 0–100; and c is 0–50; with the proviso that a, b, and c, cannot all be zero.

5. Compounds according to claim 1 in which R is n-propyl or n-octyl group.

6. Compounds according to claim 1 in which at least one Q group is an alpha methyl styryl compound.

7. Compounds according to claim 1 which are produced in a one step process.

* * * * *